US010823711B2

(12) United States Patent
Le Calve et al.

(10) Patent No.: US 10,823,711 B2
(45) Date of Patent: Nov. 3, 2020

(54) MICRO-DEVICE FOR DETECTING VOLATILE ORGANIC COMPOUNDS, AND METHOD FOR DETECTING AT LEAST ONE VOLATILE ORGANIC COMPOUND CONTAINED IN A GAS SAMPLE (71) Applicants: UNIVERSITÉ DE STRASBOURG, Strasbourg (FR); CENTRE NATIONAL DE LA RECHERCHE SCIENTIFIQUE—CNRS, Paris (FR)

(72) Inventors: Stéphane Le Calve, Rohr (FR); Rouba Nasreddine, Strasbourg (FR); Vincent Person, Strasbourg (FR); Christophe Serra, Souffelweyersheim (FR)

(73) Assignees: Universite de Strasbourg, Strasbourg (FR); Centre National de la Recherche Scientifique, Paris (FR)

( * ) Notice: Subject to any disclaimer, the term of this patent is extended or adjusted under 35 U.S.C. 154(b) by 173 days.

(21) Appl. No.: 15/533,148

(22) PCT Filed: Dec. 4, 2015

(86) PCT No.: PCT/FR2015/053339
§ 371 (c)(1),
(2) Date: Jun. 5, 2017

(87) PCT Pub. No.: WO2016/087805
PCT Pub. Date: Jun. 9, 2016

(65) Prior Publication Data
US 2017/0343517 A1 Nov. 30, 2017

(30) Foreign Application Priority Data

Dec. 5, 2014 (FR) ..................... 14 62013

(51) Int. Cl.
*G01N 30/00* (2006.01)
*G01N 30/02* (2006.01)
(Continued)

(52) U.S. Cl.
CPC ............. *G01N 30/02* (2013.01); *G01N 30/20* (2013.01); *G01N 30/62* (2013.01); *G01N 30/88* (2013.01);
(Continued)

(58) Field of Classification Search
CPC ........ G01N 30/02; G01N 30/20; G01N 30/62; G01N 30/88; G01N 33/0047
(Continued)

(56) References Cited

U.S. PATENT DOCUMENTS 4,215,564 A 8/1980 Lawson et al.
8,034,290 B1 * 10/2011 Skiba ................. G01N 27/626
422/54

(Continued)

FOREIGN PATENT DOCUMENTS

CN 2439025 Y 7/2001
CN 1793903 A 6/2006
(Continued)

OTHER PUBLICATIONS

H. K. L. Chan et al, "Multiple-Stage Microfabricated Preconcentrator-Focuser for Micro . . . ", Journal of Microelectromechanical Systems, vol. 14, No. 3, Jun. 2005, pp. 498-507.
(Continued)

*Primary Examiner* — Tarun Sinha
(74) *Attorney, Agent, or Firm* — Morgan, Lewis & Bockius LLP (57) ABSTRACT This invention relates to a micro-device for detecting volatile compounds comprising:
an input (E) and an output (S);
(Continued)

| FRENCH | ENGLISH |
|---|---|
| Prélèvement | Collection |
| Echantillonage | Sampling |
| Concentration | Concentration |
| Séparation | Separation |
| Détection | Detection |
| Air ambiant | Ambient air |
| E | Input |
| MP | Collection means |
| ME | Sampling means |
| MC | Concentration means |
| MS | Separation means |
| MD | Detection means |
| S | Output |
| Gaz vecteur | Vector gas | collection means (2) for taking a gas sample containing at least one compound to be detected;
sampling means enabling a gas volume of 100 mL or less to be sampled, arranged after the collection means;
injection means (3) of said gas sample;
separation means (5) of the compound to be detected in the gas sample;
compound detection means (6); and
a gas circulation circuit (1) located downstream of the collection means and passing through the sampling means, injection means (3), separation means (5) and detection means (6);
characterized in that the gas circulation circuit (1) has a volume of between 0.2 cm$^3$ and 2.0 cm$^3$.

13 Claims, 7 Drawing Sheets

(51) Int. Cl.
  G01N 30/20 (2006.01)
  G01N 30/62 (2006.01)
  G01N 33/00 (2006.01)
  G01N 30/88 (2006.01)
  G01N 30/08 (2006.01)
(52) U.S. Cl.
  CPC . *G01N 33/0047* (2013.01); *G01N 2030/0095* (2013.01); *G01N 2030/025* (2013.01); *G01N 2030/085* (2013.01); *G01N 2030/884* (2013.01)
(58) Field of Classification Search
  USPC .................................................. 73/23.37
  See application file for complete search history.

(56) References Cited

U.S. PATENT DOCUMENTS

| | | | |
|---|---|---|---|
| 2007/0062876 A1* | 3/2007 | Srinivasan | G01N 30/96 210/660 |
| 2009/0308136 A1* | 12/2009 | Wang | A61B 5/082 73/23.4 |
| 2011/0192214 A1 | 8/2011 | Calleri | |
| 2013/0171687 A1* | 7/2013 | Moularat | G01N 33/0029 435/34 |

FOREIGN PATENT DOCUMENTS

| | | |
|---|---|---|
| CN | 2881592 Y | 3/2007 |
| CN | 102128896 A | 7/2011 |
| CN | 103215183 A | 7/2013 |
| EP | 2045593 A2 | 4/2009 |
| EP | 2610617 A1 | 7/2013 |
| JP | 2009-047622 A | 3/2009 |
| JP | 2009-149680 A | 7/2009 |
| JP | 2011-163819 A | 8/2011 |
| JP | 2013-140154 A | 7/2013 |
| WO | 98/35940 A1 | 8/1998 |
| WO | WO 2013/039487 A1 | 3/2013 |

OTHER PUBLICATIONS

Lewis et al., "Microfabricated planar glass gas chromatography with photoionization detection," Journal of chromatography A, 1217: 768-774 (2010).

* cited by examiner

Figure 1

| FRENCH | ENGLISH |
|---|---|
| Prélèvement | Collection |
| Echantillonage | Sampling |
| Concentration | Concentration |
| Séparation | Separation |
| Détection | Detection |
| Air ambiant | Ambient air |
| E | Input |
| MP | Collection means |
| ME | Sampling means |
| MC | Concentration means |
| MS | Separation means |
| MD | Detection means |
| S | Output |
| Gaz vecteur | Vector gas |

Figure 2a

| FRENCH | ENGLISH |
| --- | --- |
| Echantillon | Sample |
| Poubelle | Waste container |
| Boucle d'échantillonage | Sampling loop |
| Moyens de séparation (MS) | Separation means (MS) |
| Gaz vecteur | Vector gas |
| Moyens de détection (MD) | Detection means (MD) |
| Position 1 | Position 1 |
| Echantillonage | Sampling |

Position 2
Injection

Figure 2b

| FRENCH | ENGLISH |
|---|---|
| Echantillon | Sample |
| Poubelle | Waste container |
| Moyens de séparation (MS) | Separation means (MS) |
| Gaz vecteur | Vector gas |
| Moyens de détection (MD) | Detection means (MD) |
| Position 2 Injection | Position 2 Injection |

Figure 3a

| FRENCH | ENGLISH |
| --- | --- |
| Vanne 1: position 1 | Valve 1: position 1 |
| Vanne 2: position 1 | Valve 2: position 1 |
| Air ambiant | Ambient air |
| Pompe | Pump |
| Poubelle | Waste container |
| Boucle d'échantillonage | Sampling loop |
| Pré-concentrateur | Pre-concentrator |
| Gaz vecteur | Vector gas |
| MS | Separation means (MS) |
| MD | Detection means (MD) |

Figure 3b

| FRENCH | ENGLISH |
|---|---|
| Vanne 1: position 2 | Valve 1: position 2 |
| Vanne 2: position 1 | Valve 2: position 1 |
| Air ambiant | Ambient air |
| Pompe | Pump |
| Poubelle | Waste container |
| Boucle d'échantillonage | Sampling loop |
| Pré-concentrateur | Pre-concentrator |
| Gaz vecteur | Vector gas |
| MS | Separation means (MS) |
| MD | Detection means (MD) |

Figure 3c

| FRENCH | ENGLISH |
|---|---|
| Vanne 1: position 1 | Valve 1: position 1 |
| Vanne 2: position 2 | Valve 2: position 2 |
| Air ambiant | Ambient air |
| Pompe | Pump |
| Poubelle | Waste container |
| Boucle d'échantillonage | Sampling loop |
| Pré-concentrateur | Pre-concentrator |
| Gaz vecteur | Vector gas |
| MS | Separation means (MS) |
| MD | Detection means (MD) |

Figure 4

| FRENCH | ENGLISH |
|---|---|
| Amplitude (Cps) | Amplitude (cps) |
| Temps | Time |
| Sens d'élution | Direction of elution |

MICRO-DEVICE FOR DETECTING VOLATILE ORGANIC COMPOUNDS, AND METHOD FOR DETECTING AT LEAST ONE VOLATILE ORGANIC COMPOUND CONTAINED IN A GAS SAMPLE

This invention relates to the detection of volatile organic compounds. More particularly, it concerns a micro-device for detecting volatile organic compounds and a method for detecting at least one volatile organic compound contained in a gas sample.

Volatile Organic Compounds (or VOCs) are organic compounds that can easily be found in gaseous form within the atmosphere.

Their volatility gives them an ability to spread more or less far from their place of emission, thus having direct and indirect impacts on humans, animals and nature.

VOCs constitute a very large family of products including BTEXs (benzene, toluene, ethylbenzene, xylenes), aromatic hydrocarbons, which are classified as being among the most dangerous.

In fact, it has been proved that toluene interferes with the central nervous system and is reprotoxic. Ethylbenze and xylenes also have harmful effects on the central nervous system. Lastly, benzene, the most dangerous of the BTEXs, is highly carcinogenic.

BTEX emissions come from different sources, for example, from using heating appliances such as gas boilers or oil stoves. Everyday consumer products such as paints and cleaning products also constitute significant additional sources.

It has been reported that average concentrations of BTEX in outdoor air can represent up to 10 $\mu g \cdot m^{-3}$ (around 3 ppb for benzene) and can reach 80 $\mu g \cdot m^{-3}$ (around 25 ppb for benzene) in indoor air.

The highly dangerous nature of these substances has led law-makers to set threshold values that must not be exceeded for the most dangerous substances such as benzene (for example, the threshold value will be 5 $\mu g \cdot m^{-3}$ for benzene in public buildings) or to suggest precautionary measures by indicating thresholds that must not be exceeded for the other BTEXs.

The very low threshold values stipulated, particularly for benzene, necessitate the use of particularly sensitive methods of measurement.

Numerous BTEX detectors adopting different methods of detection (chromatographic or spectroscopic) have therefore been developed and marketed over recent years.

Although certain detectors are efficient in terms of sensitivity, they have numerous drawbacks.

In fact, these detectors are very heavy, occupy a large amount of space and are difficult to carry. Moreover, they are expensive and have a very high consumption of gas (needed not only for the separation but also for the detection of the compounds to be detected), which in some cases can be as much as 50 mL/min.

It would therefore be advantageous to have a device for detecting volatile organic compounds that is sensitive, light, enables direct detection on site, consumes very little gas and enables fast detection.

The inventors have proved that a micro-device for detecting volatile compounds having a particular structure would be capable of meeting these requirements.

A first aim of the present invention is therefore a micro-device for detecting volatile compounds comprising:

an input and an output;
collection means for taking a gas sample containing at least one compound to be detected, arranged at the input of the micro-device;
sampling means enabling a gas volume of 100 mL or less to be sampled, arranged after the collection means;
injection means for injecting said gas sample, arranged after the sampling means;
separation means for separating the compound to be detected in the gas sample, arranged after the injection means;
compound detection means, arranged between the separation means and the output of the micro-device; and
a gas circulation circuit located downstream of the collection means and passing through the sampling means, injection means, separation means and detection means, the gas circulation circuit having a volume of between 0.2 $cm^3$ and 2 $cm^3$.

Within the context of the invention, "micro-device" means a very small, easily transportable device.

As an example, conventional laboratory devices occupy 500 $dm^3$, whereas the device according to the invention occupies only about 25 $dm^3$.

The size of the device is determined in particular by the volume of the gas circulation circuit. This volume is between 0.2 $cm^3$ and 2 $cm^3$, preferably between 0.5 $cm^3$ and 1.5 $cm^3$, and even more preferably between 0.8 $cm^3$ and 1.2 $cm^3$.

According to the invention, a "gas circulation circuit" means a "circulation circuit for the gas to be analyzed."

According to the invention, operating conditions are created such that the gas sample is near atmospheric pressure, typically between 0.5 and 1.5 bar.

In conventional devices, the volume of the gas circulation circuit is at least 8 to 10 $cm^3$.

According to the invention, the sampling means allow the sample to be collected outside the micro-device in order to introduce it into the injection means.

By way of example, this involves a sampling line comprising a pumping system that can, if required, be associated with an airflow regulation means.

According to the invention, the gas circulation circuit is located downstream of the collection means and passes through the sampling means, injection means, separation means and detection means and also includes the dead space of the different sampling, injection, separation and detection means.

The gas circulation means according to the invention does not include the collection means.

According to the invention, the gas sample collection means are arranged at the input of the micro-device. "At the input" means that the collection means can be directly coupled to the input of the micro-device or joined to the input via connection means such as ducts, capillaries or small tubes (small diameters).

Similarly, the compound detection means that are arranged between the separation means and the output of the micro-device can be directly coupled to the output of the micro-device or joined to the output via connection means such as ducts, capillaries or small tubes (small diameters).

According to the invention, the detection means enable a qualitative and quantitative analysis.

According to an embodiment, the gas sample is chosen from the group consisting in ambient air, a synthetic mixture, a sample mixture of the gas to be detected and a gaseous mixture in nitrogen, in synthetic air, in oxygen or in argon.

According to an embodiment, the compound to be detected is a volatile organic compound chosen from the group consisting in benzene, toluene, ethylbenzene, paraxylene, orthoxylene and metaxylene, as well as other unsaturated VOCs, i.e. other aromatic compounds as well as alkenes and their mixtures.

According to a particular embodiment, the compound to be detected is a volatile organic compound chosen from the group consisting in benzene, toluene, ethylbenzene, paraxylene, orthoxylene and metaxylene and their mixtures. Their low content in air and their impact on health at these levels require a very sensitive analytical method, capable of detecting on the order of a few ppb.

According to the invention, the device comprises sampling means enabling sampling of a gas volume of 100 mL or less, arranged after the collection means.

Note that the gas volume sampled cannot be zero.

Thus, according to a particular embodiment, the sampling means enable sampling of a volumes of between 10 μL and 100 mL.

Examples of sampling means include, for instance, a sampling loop. The preferably calibrated sampling loop enables the sampled gas volume to be tested.

Thus, according to a particular embodiment, the sampling means are a sampling loop having a volume of 100 mL or less, preferably between 10 μL and 100 mL.

According to a particular embodiment, the device also comprises concentration means like, for example, a pre-concentrator such as a trap, preferably microfluidic, containing one or more adsorbents.

In the context of the invention, the words "concentration" or "pre-concentration" will be used interchangeably.

The concentration means are arranged between the sampling means and the injection means.

If the device comprises concentration means, the device also comprises means enabling the sampled gas sample to be transferred to the concentration means. This may involve, for example, a multi-way valve.

If the device comprises concentration means, the gas circulation circuit is located downstream of the collection means and passes through the sampling means, these means enabling the sampled gas sample to be transferred to the concentration means, injection means, separation means and detection means and also includes the dead space of the various means of sampling, transfer, concentration, injection, separation and detection.

By way of example, in an embodiment in which the micro-device does not comprise concentration means, the sampling loop has a volume of between 10 μL and 500 μL, preferably between 50 μL and 300 μL and particularly preferably having a volume of between 100 μL and 200 μL.

According to another embodiment in which the micro-device comprises concentration means, the sampling loop has a volume of between 0.5 mL and 100 mL, preferably between 1 mL and 40 mL, and even more preferably between 5 mL and 20 mL.

The device of the present invention (with or without concentration means) is therefore characterized by sampling means enabling sampling of a volume of gas sample that is very small compared to those used in the miniaturized devices of the prior art.

This small sampling volume therefore allows the duration of sampling to be reduced without affecting the sensitivity of detection of VOCs.

The device of the invention therefore allows very fast detection of VOCs (typically less than 10 minutes).

The use of a sampling loop, with or without pre-concentration means, ensures very good repeatability and reproducibility levels.

The sampling means are connected at one end to the collection means and at the other to the injection means if the device has no concentration means or to means allowing the sampled gas sample to be transferred to the concentration means if the device has concentration means.

According to an embodiment, the injection means are a valve, preferably a multi-way valve, thus allowing not only the gas sample to be injected into the separation means but also other fluids necessary for detection to be injected therein, such as a vector gas, for example, allowing the gas sample to be conveyed into the gas circulation circuit and up to the detection means.

According to a particular embodiment, the separation means of the compound to be detected are a gas-phase micro-chromatography device comprising a micro-column.

A "gas-phase micro-chromatography device" means a gas-phase chromatography device of micrometric size, i.e. adopting a micro-column.

The gas-phase micro-chromatography device has been miniaturized. Thus, the size of the gas-phase micro-chromatography device according to the invention has been reduced by at least a factor of 20 compared to a conventional laboratory gas-phase chromatography device.

"Micro-column" means a column with an internal diameter of 0.25 mm or less, preferably less than 0.20 mm, and even more preferably less than 0.15 mm.

A person skilled in the art would be capable of finding among the polar and apolar columns a micro-column suitable for the compound to be detected.

Examples include marketed columns, such as:
  VB Wax® having the following characteristics: 100% polyethylene glycol (stationary phase); length 15 m; internal diameter 0.25 mm; film thickness 0.5 μm; and
  Rtx-624® having the following characteristics: 6% cyanopropylphenyl/94% dimethylpolysiloxane (stationary phase), length 20 m; internal diameter 0.18 mm; film thickness 1.0 μm.

According to a particular embodiment, the micro-column is an apolar or very slightly polar micro-column.

According to the invention, the micro-column is placed in an oven, preferably thermally insulated, so that the micro-column has a temperature of between 30° C. and 150° C., preferably between 50° C. and 100° C.

According to the invention, the compound detection means are not limited and correspond to all detection devices capable of being miniaturized.

According to an embodiment, the compound detection means are chosen from the group consisting in a photoionization micro-detector (PID), a spectrometer for colorimetric detection, a katharometer, a flame ionization detector (FID), a mini- or micro-mass spectrometer, an acoustic detector and an infrared detector based on tunable laser diodes.

According to a particular embodiment, the compound detection means are a photoionization micro-detector (PID) having an ionization chamber volume of between 0.1 μL and 100 μL, preferably between 1 μL and 10 μL.

The small volume of the ionization chamber of the PID micro-detector means that no additional vector gas need be added and thus reduces gas consumption while maintaining satisfactory sensitivity.

Moreover, the PID has the advantage of being very specific and very sensitive to unsaturated molecules, making it perfectly suited to the detection of BTEXs.

Another aim of this invention is a method of detecting at least one volatile compound in a gas sample comprising steps consisting in:
(i) collecting a gas sample containing the compound to be detected;
(ii) sampling the gas sample having a volume of 100 mL or less;
(iii) injecting the sample taken in step (i) and sampled in step (ii) into means enabling the separation of the compound to be detected;
(iv) separating the compound to be detected, and
(v) detecting the compound,
said method:
possibly also including a step of injecting a vector gas at step (i) and/or (ii) and/or (iii) and/or (iv) and/or (v); and
having a total vector gas consumption of between 0.1 mL/min and 5 mL/min.

According to the invention, vector gas means the gas intended to be injected into the separation means and pass through the detection means.

The method of the invention requires only a small quantity of gas, thus making it perfectly suited to measurements made directly on site. Thus, according to an embodiment, the total gas consumption is within 0.1 mL/min and 5 mL/min, preferably between 0.5 mL/min and 3 mL/min and even more preferably between 0.8 mL/min and 2.5 mL/min.

In conventional laboratory conditions, total gas consumption is at least between 20 mL/min and 250 mL/min.

According to an embodiment:
vector gas consumption during step (i), consisting in taking the gas sample containing the compound to be detected, is between 0.1 mL/min and 5 mL/min, preferably between 0.5 mL/min and 3.0 mL/min, and even more preferably between 0.8 mL/min and 2.5 mL/min;
vector gas consumption during step (ii), consisting in sampling the gas sample, is between 0.1 mL/min and 5 mL/min, preferably between 0.5 mL/min and 3 mL/min, and even more preferably between 0.8 mL/min and 2.5 mL/min;
vector gas consumption during step (iii), consisting in injecting the sample taken in step (i) and sampled in step (ii) in means enabling separation of the compound to be detected, is between 0.1 mL/min and 5 mL/min, preferably between 0.5 mL/min and 3 mL/min, and even more preferably between 0.8 mL/min and 2.5 mL/min;
vector gas consumption during step (iv), consisting in separating the compound to be detected, is between 0.1 mL/min and 5 mL/min, preferably between 0.5 mL/min and 3 mL/min, and even more preferably between 0.8 mL/min and 2.5 mL/min; and
vector gas consumption during step (v), consisting in detecting the compound, is within 0.1 mL/min and 5 mL/min, preferably between 0.5 mL/min and 3 mL/min, and even more preferably between 0.8 mL/min and 2.5 mL/min.

Thus, the method of the invention requires only a very low consumption of vector gas, required not only for the separation step but also for the injection and detection steps.

According to an embodiment, the gas sample is chosen from the group consisting in ambient air, a synthetic mixture, a standard mixture of gas to be detected and a gas mixture in nitrogen, in synthetic air, in oxygen or in argon.

According to an embodiment, the compound to be detected is a volatile organic compound chosen from the group consisting in benzene, toluene, ethylbenzene, paraxylene, orthoxylene and metaxylene, as well as other unsaturated VOCs, i.e. the other aromatic compounds, as well as alkenes and their mixtures.

According to a particular embodiment, the compound to be detected is a volatile organic compound chosen from the group consisting in benzene, toluene, ethylbenzene, paraxylene, orthoxylene and metaxylene and their mixtures.

According to another embodiment, the gas sample containing the compound to be detected at step (i) is taken using a pumping system capable of being connected, if necessary, to an airflow regulation means.

According to an embodiment, sampling step (ii) is performed using sampling means, such as a sampling loop, preferably calibrated.

Note that the sampled volume cannot be zero.

Thus, according to a particular embodiment, the sampled volume is between 10 µL and 100 mL.

According to a particular embodiment, the volume of the sampling loop is between 10 µL and 500 µL, preferably between 50 µL and 300 µL and particularly preferably between 100 and 200 µL.

According to another particular embodiment, the method includes a step of pre-concentration after step (ii) in order to increase the detection limit.

According to the particular embodiment in which the method includes a pre-concentration step, the volume of the sampling loop is between 0.5 mL and 100 mL, preferably between 1 mL and 40 mL, and even more preferably between 5 mL and 20 mL.

According to the invention, the transfer of the sampled volume to the concentration means is achieved with the aid of a transfer gas.

According to an embodiment, the transfer gas is the vector gas intended to be injected into the separation means.

According to this embodiment, the transfer gas is not included in the total vector gas consumption in the method according to the present invention.

The transfer gas and vector gas can therefore have different flow rates.

Thus, according to an embodiment, transfer of the sampled volume to the concentration means is achieved using a transfer gas having a flow rate of between 0.1 mL/min and 100 mL/min, preferably between 0.2 mL/min and 40 mL/min and even more preferably between 1 mL/min and 20 mL/min. By way of example, in the case of a sample of 5 mL, it may for example be transferred at 2.5 mL/min for 2 min.

The method of the present invention (with or without the pre-concentration step) is therefore characterized by sampling performed in sampling means, for example a sampling loop having a very small volume compared to those used in the known methods of the prior art.

This small sampling volume therefore allows the sampling time to be reduced without affecting VOC detection sensitivity.

The method of the invention therefore enables very quick VOC detection times (typically less than 10 minutes).

The use of a sampling loop, with and without a pre-concentration step, ensures very good repeatability and reproducibility levels.

According to a particular embodiment, injection step (iii) is achieved using a valve, preferably a multi-way valve, thus making it possible not only to inject the gas sample but also to inject other fluids necessary for detection, such as a vector gas, allowing the gas sample to be conveyed during detection.

The injection of vector gas at a constant flow rate can be achieved with any flow- and pressure-regulation means, for example with a pressure regulator located upstream of the column, or with a mass flow regulator.

The vector gases according to the invention are not limited.

Thus, according to an embodiment, the vector gas can be hydrogen, nitrogen or even a rare gas.

According to a particular embodiment, the vector gas is chosen from the group consisting in hydrogen, nitrogen, helium, argon and their mixtures.

According to a particular embodiment, the separation of the compound is achieved using a gas-phase micro-chromatography device adopting a micro-column.

A person skilled in the art will be capable of finding among the polar and apolar columns a micro-column suitable for the compound to be detected.

Examples include marketed columns, such as:

VB Wax® having the following characteristics: 100% polyethylene glycol (stationary phase); length 15 m; internal diameter 0.25 mm; film thickness 0.5 μm; and Rtx-624® having the following characteristics: 6% cyanopropylphenyl/94% dimethylpolysiloxane (stationary phase), length 20 m; internal diameter 0.18 mm; film thickness 1.0 μm.

According to a particular embodiment, the micro-column is an apolar or very slightly polar micro-column.

According the invention, the micro-column is placed in an oven, preferably thermally insulated, so that the micro-column has a temperature of between 30° C. and 150° C., preferably between 50° C. and 100° C.

As previously indicated, the vector gases according to the invention can be chosen from the group consisting in hydrogen, nitrogen, helium, argon and any other rare gas. They are adapted to suit the column used, the volatile organic compounds to be detected, the analysis times, etc.

According to a particular embodiment, the vector gas is hydrogen since it has been proved by the inventors that this vector gas enables advantageously reduced detection times and an increase in the height of the chromatogram peaks relating to the different BTEXs.

According to an embodiment, the gas-phase micro-chromatography is performed with an elution flow rate of between 0.1 mL/min and 5 mL/min of vector gas. It has been proved by the inventors that when nitrogen is used as a vector gas, the optimum flow rate is 1 mL/min and that, when hydrogen is used as a vector gas, the optimum flow rate is 2 mL/min.

According to an embodiment, the compound is detected with a detector chosen from the group consisting in a spectrometer for colorimetric detection, a katharometer, a flame ionization detector (FID), a mini- or micro-mass spectrometer, an acoustic detector and an infrared detector based on tunable laser diodes.

According to a particular embodiment, the compound is detected with a photoionization micro-detector (PID) having an ionization chamber volume of between 0.1 μL and 100 μL, preferably between 0.5 μL and 10 μL.

The small volume of the ionization chamber of the PID micro-detector means that no additional vector gas need be added and thus reduces gas consumption while maintaining satisfactory sensitivity.

Moreover, the PID has the advantage of being very specific and very sensitive to unsaturated molecules, making it perfectly suited to the detection of BTEXs.

It has been shown that the method of the invention, even without the pre-concentration step, allows detection limits for benzene to be obtained that are below the legally required levels, namely 1 ppb (3 μg/m$^3$) when the vector gas is hydrogen.

The method of the invention with a pre-concentration step allows even lower detection limits to be obtained, below 0.1 ppb.

Thus, it has been proved that the detection micro-device of the present invention simultaneously comprises the following characteristics:

very high sensitivity and high precision even at very low contents of the compounds to be detected;

light and very compact, enabling it to be transported between two analysis sites;

very low gas consumption, and fast detection (in 10 minutes).

This is why the device of the invention or the method of the invention are perfectly adapted for measurements made directly on site in order to detect any sources (leaks in an industrial environment, etc.) of BTEXs, even at very low concentrations.

Another aim of the present invention is therefore to use a micro-device such as previously defined or the method such as previously defined in order to detect compounds chosen from the group consisting in benzene, toluene, ethylbenzene, paraxylene, orthoxylene and metaxylene, particularly in closed environments, and more particularly in public buildings (schools, nurseries, etc.).

A clearer understanding of the invention will emerge from the accompanying drawings, in which.

Figure 1:
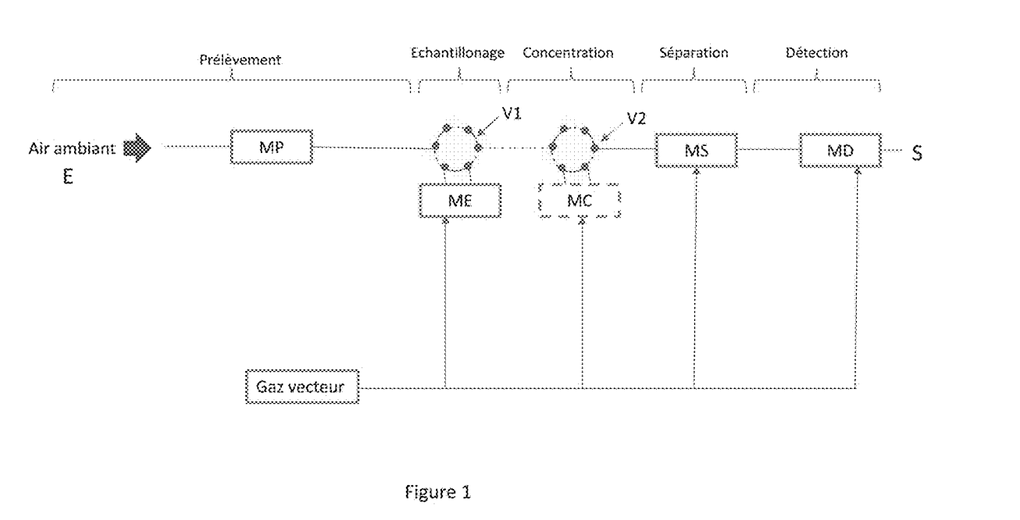
FIG. 1 is a descriptive diagram of a micro-device according to an embodiment of the invention.

The micro-device shown in FIG. 1 comprises an input E and an output S and a gas-circulation circuit beginning after the collection means and passing through the sampling means ME (for example a sampling loop), concentration means, if applicable, (for example a pre-concentrator), injection means (for example a 6-way valve V1 without a pre-concentrator or V2 with a pre-concentrator), separation means MS for the compound to be detected (for example a micro-chromatography device comprising a micro-column arranged in an oven) and compound detection means (for example a photoionization micro-detector). The gas circulation circuit is in particular characterized by its small volume of between 0.2 cm$^3$ and 2 cm$^3$, preferably between 0.5 cm$^3$ and 1.5 cm$^3$. Upstream of the gas circulation circuit are the collection means MP for collecting a gas sample (in this case, ambient air) containing at least one compound to be detected, which are arranged at the input of the micro-device. According to an embodiment, the collection means MP are a collection line on which is installed a pump connected to an airflow regulator.

The sampling means ME located after the collection means MP are connected to a six-way valve V1.

The 6-way valve V1 is used in order to inject the gas sample from the collection means towards the separation means or to transfer the gas sample from the collection means towards the concentration means (depending on whether the micro-device has concentration means) but also to inject other fluids necessary for separation and detection such as a vector gas.

The sampling loop allows a volume of gas of 100 mL or less, preferably between 10 μL and 100 mL, to be sampled.

When the micro-device has no pre-concentration means MC, the 6-way valve V1 allows the sample to be injected directly into the separation means MS. The valve V1 in this case fulfills the role of injection means.

When the micro-device has pre-concentration means MC, the valve V1 allows the sampled gas volume to be transferred to the pre-concentration means MC.

In this case, the injection means are represented by a second valve V2 allowing the pre-concentrated sample to be injected towards the separation means MS. The separated gas sample is then detected by the detection means MD.

Figure 2A:
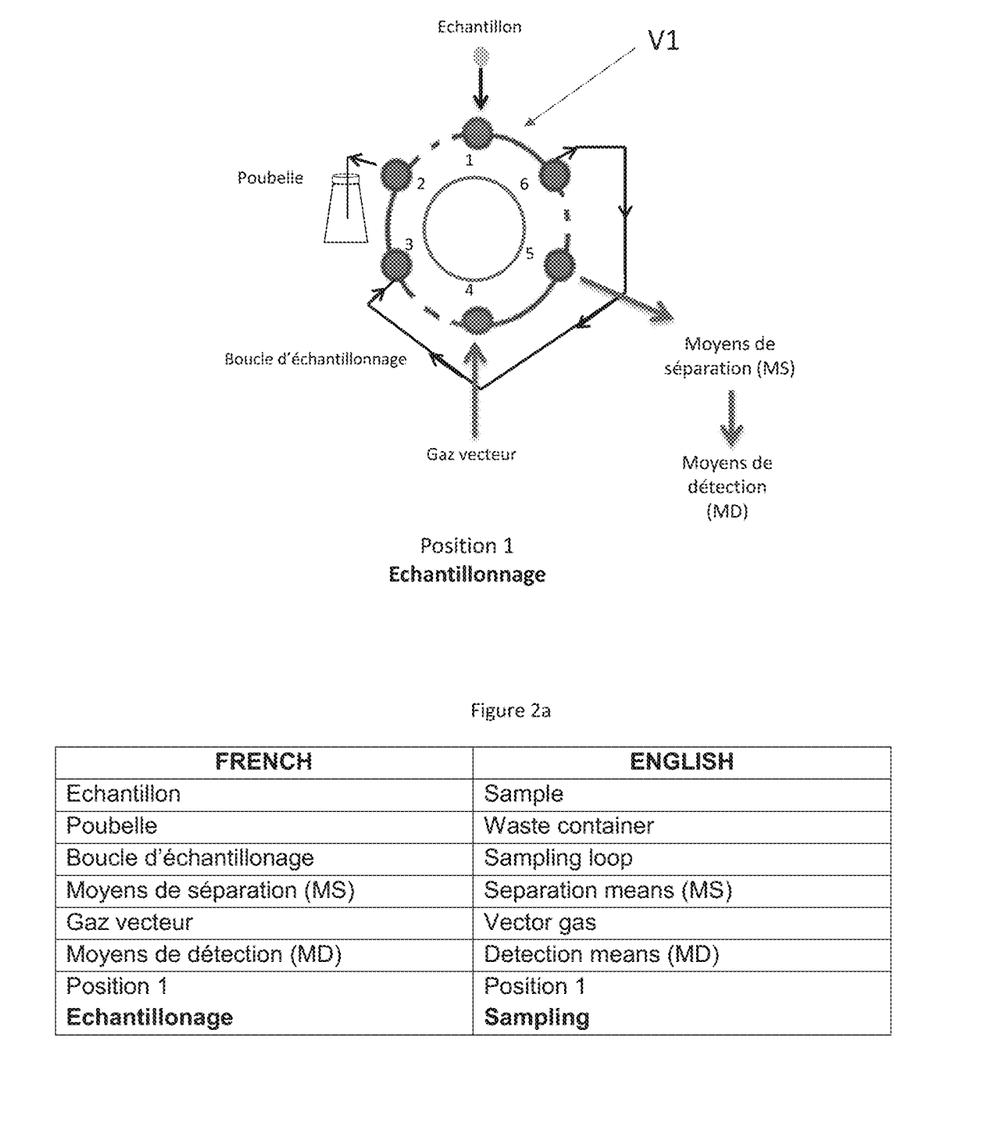
FIGS. 2a and 2b represent the different steps of the detection method according to an embodiment without the pre-concentration step.
Figure 2B:
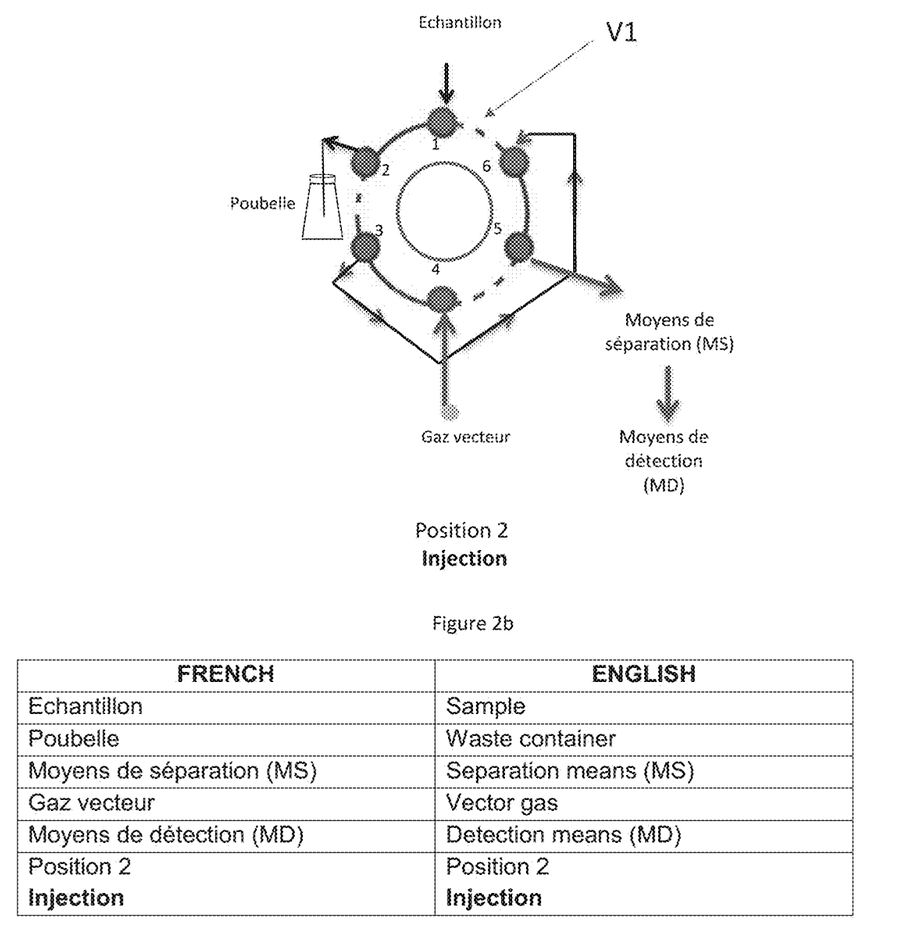

FIG. 2 shows the different steps of the method according to an embodiment in which the method does not include a pre-concentration step.

The first step consists in taking and sampling the gas sample (FIG. 2a).

The valve V1 is in position 1 in order to sample the gas sample in a sampling loop having a volume of between 10 μL and 500 μL, preferably between 50 μL and 300 μL and particularly preferably between 100 and 200 μL.

For this, the sample to be analyzed is introduced into way 1 of the valve V1 and exits through way 6 in order to pass through the sampling loop connected to ways 6 to 3.

Valve V1 also allows a vector gas (entering through way 4 and exiting through way 5) into the separation (MS) and detection (MD) means but also allows the undesirable compounds to be rejected (way 2).

The second step involves injecting the gas sample towards the separation means, then detecting the separated sample by the detection means (FIG. 2b where the valve V1 is in injection position 2).

For this, the sample sampled in the sampling loop emerges through way 6 and is injected into the separation means through way 5 where the vector gas required for the separation and detection of the gas sample is also introduced.

Figure 3A:
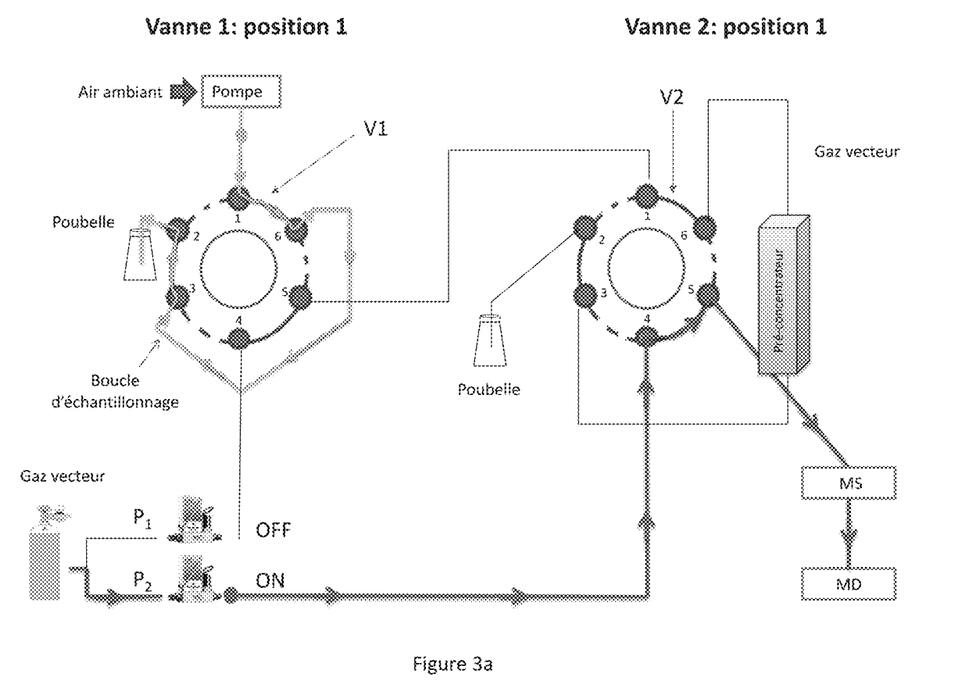
FIGS. 3a to 3c represent the different steps of the detection method according to another embodiment with a pre-concentration step.
Figure 3B:
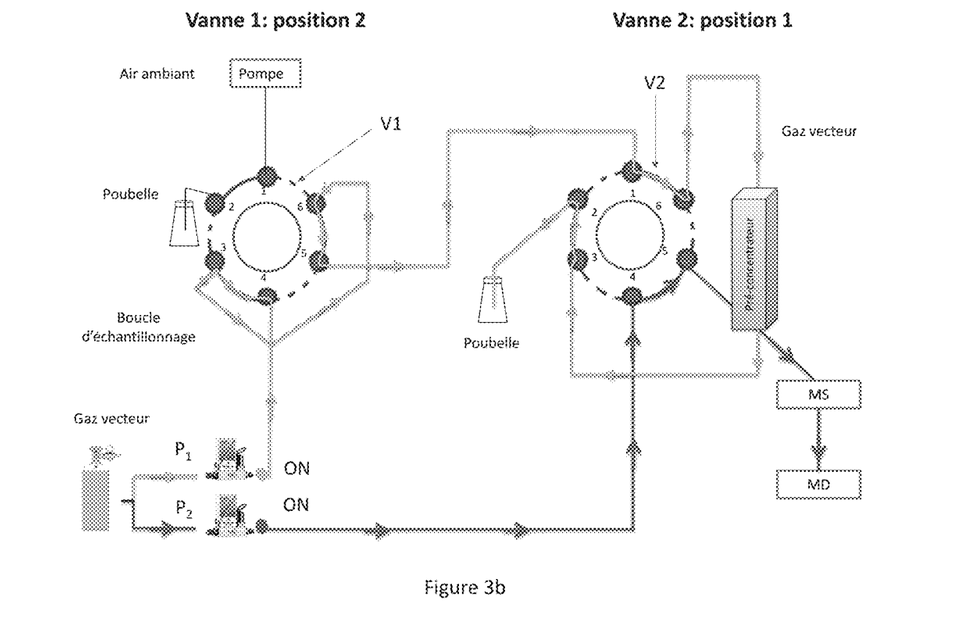
Figure 3C:
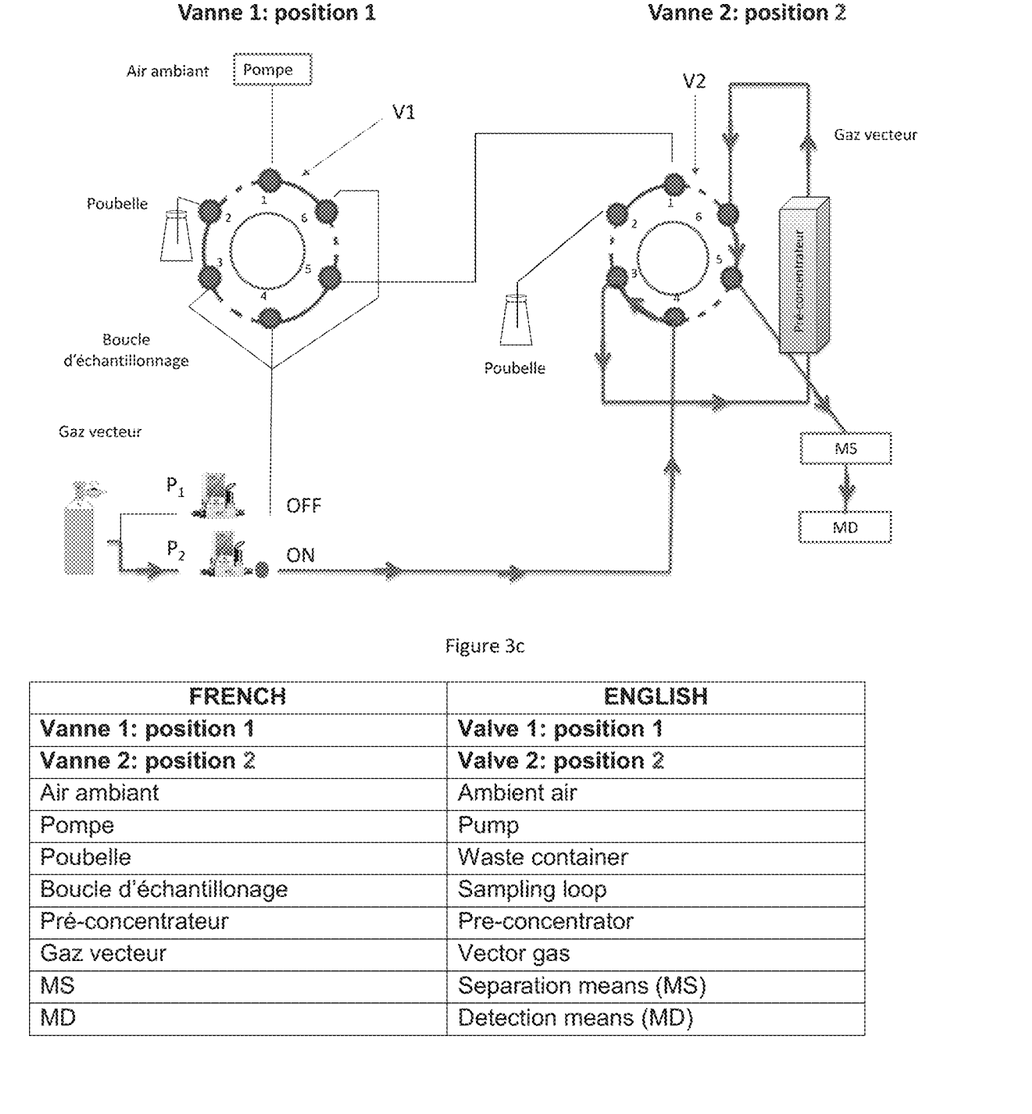

FIG. 3 represents the different steps of the method according to an embodiment where the method comprises a pre-concentration step.

The first step involves taking and sampling the gas sample (FIG. 3a).

Valve V1 is in position 1 in order to sample the gas sample in the sampling loop having a volume of between 0.5 mL and 100 mL, preferably between 1 mL and 40 mL, and even more preferably between 5 mL and 20 mL.

For this, the sample to be analyzed is introduced into way 1 of valve V1 and exits via way 6 in order to pass through the sampling loop connected to ways 6 to 3.

Valve V2 is in position 2 and allows the separation means (MS) and detection means (MD) to be supplied with vector gas. Vector gas is introduced into V2 through way 4 and exits through way 5 in order to supply the separation and detection means.

The second step (FIG. 3b) involves transferring the sampled gas volume to the pre-concentration means. Valve 1 is therefore in position 2 during this step and thus allows the gas volume to be transferred by means of said gas which itself is used as vector gas and is necessary for this transfer. The flow rate used during this transfer can be substantially different from that of the vector gas passing into the separation means (a micro-column for example).

During this step, the sample sampled in the sampling loop connected to ways 3 to 6 is transferred to the concentration means via the same gas as that used as a vector gas entering through way 4 of V1. The sampled sample then exits through way 5 of V1 and is introduced into valve V2 through way 1 in order to be introduced into the concentration means via way 6 of V2.

The transfer of the sampled volume towards the concentration means is achieved at a flow rate of between 0.1 mL/min and 100 mL/min, preferably between 0.2 mL/min and 40 mL/min and even more preferably between 1 mL/min and 20 mL/min.

Valve V2 is still in position 2 and can supply the separation (MS) and detection (MD) means with vector gas (the vector gas enters through way 4 of V2 and exits towards the separation means through way 5 of V2).

Lastly, the third step (FIG. 3c) involves injecting the pre-concentrated gas sample towards the separation means MS then detecting the separated sample by the detection means MD.

Valve then passes back to position 1 and valve 2 is in position 2.

During this step, the vector gas enters through way 4 of valve V2, exits through way 5 in order to pass through the pre-concentrator conveying with it the pre-concentrated gas sample, which enters through way 6 of V2 and exits through way 5 of V2 towards the separation means.

EXAMPLE: SEPARATION AND DETECTION OF DIFFERENT BTEX COMPOUNDS

In this example, the following compounds have been separated and detected according to the method of the present invention:
1: Benzene
2: Toluene
3: Ethylbenzene
4: Meta- and para-xylenes
5: Orthoxylene Detection of the compounds contained in the generated synthetic air has been achieved with the aid of the device as described in FIG. 1, according to the following steps:
(i) the generated synthetic air comprising all of compounds (1)-(5) is taken with the aid of a pump at a flow rate of 10 to 50 mL/min, then injected into a sampling loop for a period ranging from 5 seconds to 10 min so as totally to renew the air contained in the sampling loop;
(ii) the sample exiting the sampling loop is then injected into a gas-phase micro-chromatography micro-column arranged in an oven, with the aid of a 6-way valve that simultaneously also injects hydrogen as the vector gas into the micro-column so that the sample is conveyed into the column by the vector gas.

Technical Characteristics of the Separation Step:
micro-column: RTX-624®
elution flow rate: 2.5 mL/min of hydrogen
column temperature: 70° C.
(iii) the sample is then detected with a photoionization micro-detector (PID).

Figure 4:
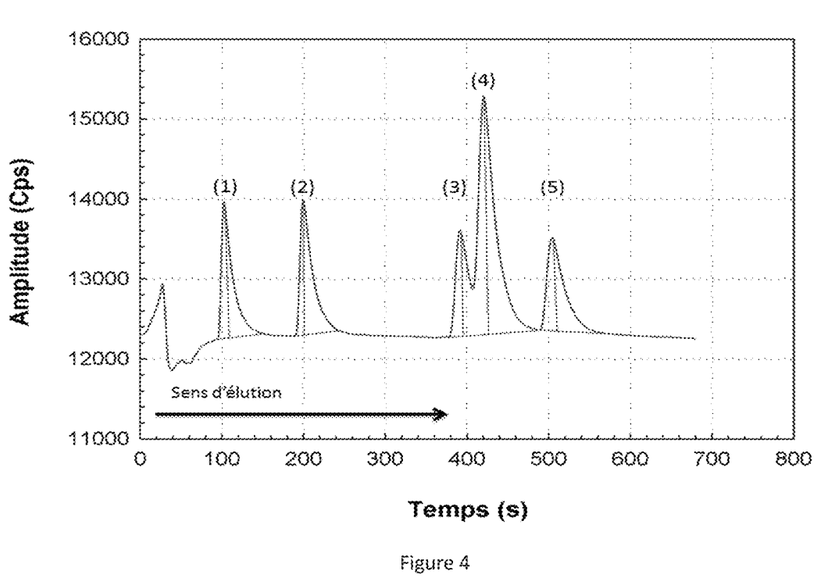
FIG. 4 is a chromatogram showing the separation of 100 ppb of BTEX compounds.

FIG. 4 represents the chromatogram obtained on implementing the method previously described.

It reveals that the most volatile compounds (benzene 1, toluene 2) exit first and the heaviest last (ethylbenzene 3 and the xylenes: meta- and para-xylenes being co-eluted 4 and orthoxylene 5).

This detection method thus enables a rapid quantitative analysis (in less than 10 minutes) of the BTEXs and requires only a small quantity of vector gas (2.5 mL/min in the example shown in FIG. 4).

The invention claimed is:

1. Micro-device for detecting volatile compounds comprising:
    an input and an output;
    a collection means for taking a gas sample containing at least one compound to be detected, arranged at the input of the micro-device;
    a sampler enabling a gas volume of between 10 pL and 500 pL to be sampled, arranged after the collection means;
    an injection means for injecting said gas sample, arranged after the sampling loop;
    a separation means for separating the compound to be detected in the gas sample, arranged after the injection means;
    a compound detection means, arranged between the separation means and the output of the micro-device, where the compound detection means is a photoionization micro-detector; and
    a gas circulation circuit located downstream of the collection means and passing through the sampling loop, injection means, separation means and detection means,
    wherein the gas circulation circuit has a volume of between 0.2 cm$^3$ and 2.0 cm$^3$.

2. Detection micro-device according to claim 1, wherein the separation means of the compound to be detected are a gas-phase microchromatography device comprising a micro-column.

3. Method of detecting at least one volatile compound in a gas sample comprising:
    (i) collecting a gas sample containing the compound to be detected;
    (ii) sampling the gas sample having a volume of 100 mL or less, said sampling being performed in a sampling loop;
    (iii) injecting the sample taken in step (i) and sampled in step (ii) into means enabling the separation of the compound to be detected;
    (iv) separating the compound to be detected, and
    (v) detecting the compound,
    said method optionally also including a step of injecting a vector gas at step (i) and/or (ii) and/or (iii) and/or (iv) and/or (v),
    wherein the total vector gas consumption is between 0.1 mL/min and 5 mL/min.

4. Method according to claim 3, wherein the sampling step (ii) is performed using sampling loop having a volume of between 10 μL and 500 μL.

5. Method according to claim 3, wherein the method includes a step of pre-concentration after step (ii).

6. Method according to claim 5, wherein the sampling step (ii) is achieved using a sampling loop having a volume of between 0.5 mL and 100 mL.

7. Method according to claim 5, wherein the transfer of the sampled volume to the concentration means is achieved using a transfer gas at a flow rate of between 0.1 mL/min and 100 mL/min.

8. Method according to claim 3, wherein the separation of the compound to be detected in step (iii) is achieved using a gas-phase micro-chromatography device comprising a micro-column.

9. Method according to claim 8, wherein the vector gas used during separation by gas-phase micro-chromatography is selected from the group consisting of hydrogen, nitrogen, helium, argon and their mixtures.

10. Method according to claim 8, wherein the gas-phase micro-chromatography is performed with an elution flow rate of between 0.1 mL/min and 5 mL/min.

11. Method according to claim 3, wherein compound detection is achieved using a detector selected from the group consisting of a photoionization micro-detector (PID), a spectrometer for colorimetric detection, a katharometer, a flame ionization detector (FID), a mini- or micro-mass spectrometer, an acoustic detector and an infrared detector based on tunable laser diodes.

12. Method according to claim 3, wherein the volatile compound to be detected is selected from the group consisting of benzene, toluene, ethylbenzene, paraxylene, orthoxylene and metaxylene.

13. Use of the micro-device as defined in claim 1 or of the method as defined in claim 3 to detect compounds selected from the group consisting of benzene, toluene, ethylbenzene, paraxylene, orthoxylene and metaxylene.

* * * * *